United States Patent [19]

Coulter

[11] 3,930,736
[45] Jan. 6, 1976

[54] APERTURE TUBE WITH ATTACHED THIEF

[75] Inventor: Wallace Coulter, Miami Springs, Fla.

[73] Assignee: Coulter Electronics, Inc., Hialeah, Fla.

[22] Filed: July 1, 1974

[21] Appl. No.: 484,581

[52] U.S. Cl. ............................. 356/246; 324/71 CP
[51] Int. Cl.² .......................................... G01N 1/10
[58] Field of Search ..................... 356/40, 73, 246; 324/71 CP

[56] References Cited
UNITED STATES PATENTS

| | | | |
|---|---|---|---|
| 3,743,424 | 7/1973 | Coulter | 356/40 X |
| 3,746,976 | 7/1973 | Hogg | 324/71 CP |
| 3,746,977 | 7/1973 | Hogg | 324/71 CP |

*Primary Examiner*—Vincent P. McGraw
*Attorney, Agent, or Firm*—Silverman & Cass, Ltd.

[57] ABSTRACT

An apparatus used in a particle measuring device where liquid suspensions of particles to be measured are brought into contact with the apparatus. The apparatus includes an aperture tube and a thief conduit which are secured to one another and form a unitary structure. The unitary structure has its exterior surface constructed and arranged so as to minimize contamination via carry over from one suspension to another.

12 Claims, 3 Drawing Figures

APERTURE TUBE WITH ATTACHED THIEF

CROSS REFERENCE TO RELATED PATENTS

The apparatus described herein can be employed in the apparatus shown and described in U.S. Pat. No. 3,743,424 which is owned by the same assignee, and which is incorporated herein by this reference to the extent necessary.

BACKGROUND OF THE INVENTION

In apparatus such as disclosed in the above noted patent an electronic particle counting device operating on the Coulter principle is combined with an optical hemoglobinometer such that at some step in the sequence of events of the operation of the counting device, the operation of the optical hemoglobinometer is started. The same sample suspension that is utilized in the counting device is also utilized in the hemoglobinometer by means of a fluid connection from the counting device to the hemoglobinometer so that there is no need to handle the sample twice.

The electronic particle counting device includes an aperture tube such as is commonly known in the art. The fluid connection to the hemoglobinometer is, in the above identified patent, by means of a thief, hereinafter termed a thief conduit. In operation, a liquid suspension of particles is placed in a beaker which is brought into contact with the aperture tube and thief conduit. When the analysis of the liquid supsension is complete, the beaker with remaining liquid suspension is removed and another beaker with a new liquid suspension to be analyzed is brought into contact with the aperture tube and thief conduit so that the analyzing cycle can be repeated.

When the first beaker is removed, a small amount of the liquid suspension can adhere to the exterior surface of the aperture tube and thief conduit. This small amount of liquid suspension will carry over to the liquid suspension in the next beaker, slightly contaminating that liquid suspension and possibly affecting the results of the analysis process. Minimizing this carry over would be extremely desirable.

If the thief conduit draws suspension from the same height in the suspension as the aperture in the aperture tube, it can be assumed that the particles being counted are substantially the same as those being passed through the optical hemoglobinometer. As a result, the probability of a correct analysis is statistically increased. Much time and effort must be spent by a technician to properly align the aperture tube and thief conduit so that when liquid suspension is brought into contact with the aperture tube and thief conduit, they will be at the same height in the liquid suspension. Furthermore, the apparatus must be regularly checked to ensure continued proper alignment, causing a continued expenditure of effort on unproductive activity.

If the aperture tube and thief conduit are positioned at the same height in a suspension, the draw of fluid by the thief conduit can disturb the fluid adjacent the aperture in the aperture tube. if the fluid is disturbed the particle count can be adversely affected. The technician, in setting up the equipment, must exercise great care to ensure that the aperture tube and thief conduit are positioned so as to reduce the possibility of one affecting the operation of the other. Again, there is a continued expenditure of time and effort on what can be considered unproductive activity.

SUMMARY OF THE INVENTION

In practicing this invention an apparatus is provided for use in a particle measuring device where liquid suspensions of particles to be measured are brought into contact with the apparatus. The liquid suspensions can adhere to the apparatus and carry over from one suspension to another causing contamination. The apparatus includes an aperture tube and a thief conduit which are attached to one another and form a unitary structure. This unitary structure has its exterior surface constructed and arranged to minimize carry over from one liquid suspension to another.

In one embodiment, the aperture tube and thief conduit outer surfaces are attached along a line forming a junction between the two. The exterior surfaces of the aperture tube and thief conduit form a V shaped depression on each side of this junction. the V shaped depression is filled with material so as to form a substantially smooth exterior surface, thus minimizing the possibility of carry over.

In a second embodiment, the thief is elongate and is positioned in the aperture tube. The opposite ends of the thief conduit open through the walls of the aperture tube to the exterior of the aperture tube.

DESCRIPTION OF THE PREFERRED EMBODIMENTS

Figure 1:
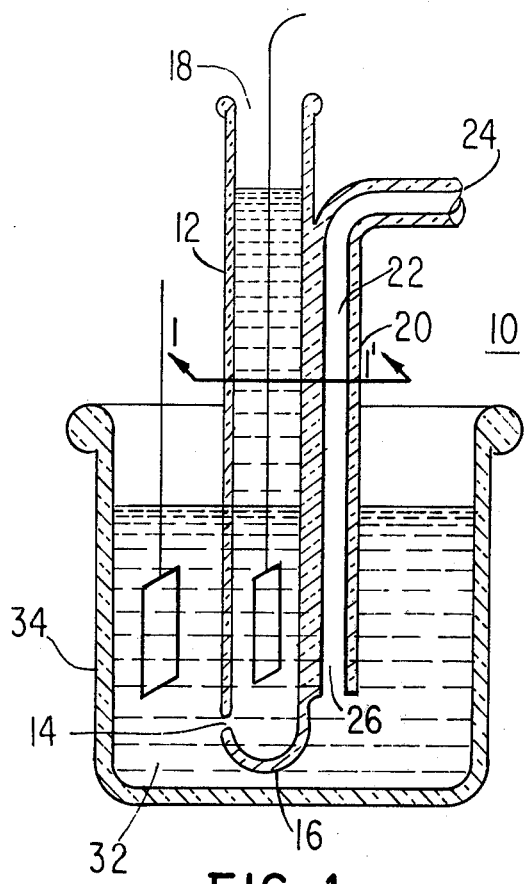
FIG. 1 is a section view showing one embodiment of the aperture tube and attached thief of this invention.
Figure 3:
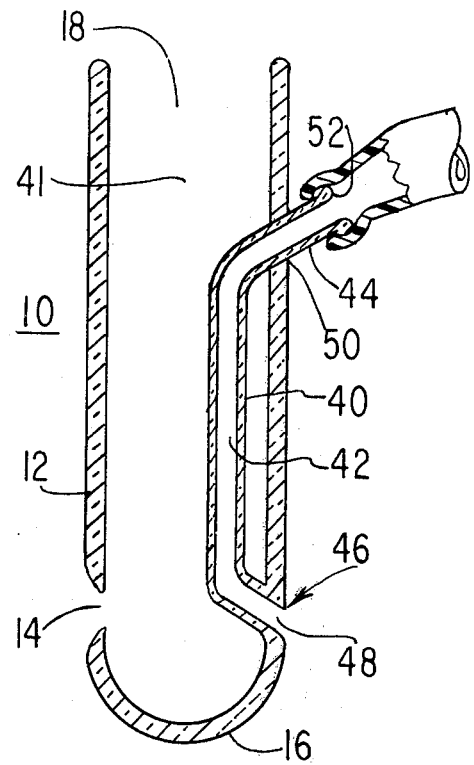
FIG. 3 is a section view of another embodiment of the aperture tube and attached thief of this invention.
Figure 2:
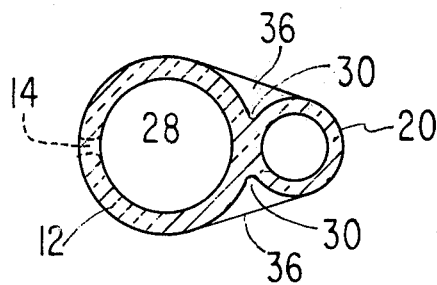
FIG. 2 is a cross section of the aperture tube and attached thief along the lines 1—1 of FIG. 1.

Referring to FIGS. 1 and 2, there is shown an aperture tube with attached thief conduit 10. The aperture tube with attached thief conduit 10 includes an elongate cylindrical aperture tube 12 with an aperture 14 formed in the side wall thereof. Aperture tube 12 is of the type well known in the art, reference being made to U.S. Pat. No. 2,656,508 for a more detailed description of the aperture tube itself. It is sufficient to further identify only bottom end 16, which is closed, and open top end 18 of aperture tube 12.

A thief conduit 20 has a bore 22 passing therethrough, and an open top and bottom end 24 and 26, respectively. Open end 24 attaches to an optical hemoglobinometer such as is shown in the above noted U.S. Pat. No. 3,743,424. Thief conduit 20 and aperture tube 12 are attached to one another along a line forming a junction and identified generally at 28 in FIG. 2. The side walls of aperture tube 12 and conduit thief 20, on each side of junction 28, form V shaped depressions 30.

When aperture tube and attached thief conduit 10 is inserted into a liquid suspension of particles such as suspension 32 in beaker 34, a small amount of the liquid suspension 32 will adhere to the surfaces of V shaped depressions 30. When aperture tube and attached thief conduit is removed from suspension 32 and then inserted into the next or following liquid suspension, the portion of liquid suspension 32 adhering to the side walls of V shaped depressions 30 will be carried over to the new liquid suspension, contaminating that liquid suspension.

In order to eliminate this problem, material 36 is formed in V shaped depressions 30, filling the depressions and resulting in a smooth circular or eliptical external surface. By providing a smooth external surface and eliminating unusual contours such as V shaped depressions 30, the external surface is constructed and arranged to minimize carry over of liquid suspension from one suspension to another. Furthermore, by smoothing out the external surface of aperture tube and thief conduit 10, the external surface area is minimized thus minimizing the contact area with liquid suspension 32 and the carry over which can result from the adhesion to the surface area itself.

The aperture tube 12, thief conduit 20 and material 36 must be impervious to deterioration when brought into contact with different types of liquid suspension. In the preferred embodiment, aperture tube 12, conduit tube 20 and material 36 are glass. Material 36 will be formed by the V shaped depressions as the aperture tube 12 and the conduit 20 are formed resulting in a unitary structure.

Although aperture tube 12 and thief conduit 20 are shown as having a circular configuration in FIG. 2, it is to be understood that they need not be perfectly circular. In fact, it may be found preferable that they not be circular but rather ellipsoidal so that when formed together with material 36 filling the V shaped depressions formed by the junction, the entire outer surface will be circular in shape when viewed from the top end as in FIG. 2. A circular exterior surface will provide the minimum surface area for contact with liquid suspension 32.

In the embodiment shown in FIGS. 1 and 2, thief conduit 20 is secured to aperture tube 12 such that bottom end 26 is at substantially the same height in liquid suspension 32 as aperture 14. This allows liquid suspension to be drawn into bore 22 of thief conduit 20 which is substantially the same as the liquid suspension entering aperture 14, so that the particles counted will be substantially the same as those being passed through the optical hemoglobinometer attached to top end 24 of thief conduit 20. In addition, thief conduit 20 is secured to aperture tube 12 along a line substantially radially opposite to aperture 14. By positioning thief conduit 20 substantially radially opposite to aperture 14 the fluid drawn into bottom end 26 of thief conduit 20 will not disturb the liquid suspension surrounding aperture 14 so that the particle count, based upon particles passing through aperture 14 will not be detrimentally affected.

Refferring now to FIG. 3, another embodiment of the aperture tube and attached thief conduit of this invention is shown generally at 10. An elongate cylindrical aperture tube 12 is again shown having an aperture 14 positioned in the side wall thereof. Aperture tube 12 has a closed bottom end 16 and open top end 18 as shown in FIGS. 1 and 2. A thief conduit 40, having a bore 42 passing therethrough, is positioned in the interior 41 of aperture tube 12. The top end 44 and the bottom end 46 extend through the side wall of aperture tube 12. In the embodiment shown, end 46 of thief conduit 40 terminates at an opening 48 in the side wall of aperture tube 12 with the axis of bore 42 axially aligned with opening 48. Top end 44 of thief conduit 40 passes through the side wall of aperture tube 12 at a point 50 and terminates at a point 52 beyond side wall of aperture tube 50. This allows end 44 to be attached to the optical hemoglobinometer such as shown in the above noted U.S. Pat. No. 3,743,424.

The connection between thief conduit 40 and opening 48 in the side wall of aperture tube 12 is fluid tight so that liquid suspension entering opening 48 will only pass through bore 42 and will not enter interior 41 of aperture tube 12. The connection between thief conduit 40 and aperture tube 12 at 50 is also fluid tight preventing any liquid suspension in the interior 41 of aperture tube 12 from escaping.

Again, as with the embodiments shown in FIGS. 1 and 2, aperture tube 12 and thief conduit 40 are glass. The opening 48 in the side wall of aperture tube 12 is substantially radially opposite to aperture 14 and is located at substantially the same height below open end 18 of aperture tube 12 as aperture 14, both for the same reasons noted above with respect to the embodiment shown in FIGS. 1 and 2.

By positioning thief conduit 40 internal to aperture tube 12, the only surface area to which liquid suspension could adhere is the exterior surface of aperture tube 12 itself. Any suspension which adheres to the side walls of thief conduit 40 would not affect or contaminate a subsequent suspension into which aperture tube 12 is placed because the suspension adhering to thief conduit 40 would only contaminate the new suspension after the suspension has passed through aperture 14 and has been counted. Once the counting has occurred, contamination is of no consequence. Furthermore, positioning thief conduit 20 internal to aperture tube 12 minimizes the external surface area and eliminates unusual external contours so as to minimize the possibility of carry over from one liquid suspension to another.

As can be seen, an aperture tube with attached thief conduit has been provided for use in a particle measuring device. The unitary structure minimizes external surface area, thus minimizing the possibility of carry over of liquid suspension. By combining the aperture tube and thief, problems associated with placing them in contact with a suspension to be measured at substantially the same height and in a position such that the action of one does not affect the action or operation of the other are substantially reduced.

What it is desired to secure by Letters Patent of the United States is:

1. an apparatus for use in a particle measuring device wherein liquid suspensions of particles to be measured are brought into contact with the apparatus and wherein the liquid suspensions can adhere to the apparatus and carry over from one suspension to another causing contamination, the apparatus including in combination, an aperture tube having a top end, a bottom end and an aperture formed therein a predetermined height below said top end, a thief conduit attached to said aperture tube and forming a unitary structure therewith for reducing exterior surface area whereby said unitary structure minimizes carry over from one suspension to another for that portion of the unitary structure brought into contact with said liquid suspensions of particles.

2. The apparatus of claim 1 wherein said unitary structure is further constructed and arranged to have a substantially minimum total exterior surface area for exposing a minimum surface area to said liquid suspension whereby carry over for that portion of the unitary structure brought into contact with said liquid suspensions of particles is minimized.

3. the apparatus of claim 1 wherein said thief conduit has an open bottom end, the aperture tube aperture and the open bottom end of said thief conduit veing located at substantially the same height below said top end on said apparatus.

4. the apparatus of claim 1 wherein said aperture tube has at least a first radius extending from the center of said tube to the aperture and said thief conduit is secured to said aperture tube along a line substantially radially opposite the aperture tube aperture.

5. The apparatus of claim 1 wherein said aperture tube is an elongate cylinder having a first thief opening formed therein, said thief conduit having a first thief end secured to the periphery of said first opening and extending interior said aperture tube from said first end to a point a predetermined distance above said first end, said thief conduit passing through said cylinder from interior to exterior at said second point and terminating at a second end exterior to said aperture tube.

6. The apparatus of claim 1 wherein said aperture tube and thief conduit are each elongate cylinders and are attached to one another at their outer surfaces and at substantially a single line along the length thereof to form a junction, said cylinders forming a substantially V shaped depression on each side of said junction, and wherein material substantially fills said V shaped depression and forms a portion of said exterior surface for minimizing carry over of said liquid suspension in said V shaped depression.

7. The apparatus of claim 6 wherein said aperture tube, thief conduit and material are glass.

8. The apparatus of claim 1 wherein said aperture tube is an elongate cylinder having an open top end and a closed bottom end, said cylinder having a first thief opening formed therein, said thief conduit having a first end secured to the periphery of said first thief opening with said thief conduit bore being axially aligned with said thief opening, said thief conduit extending from said first end towards said aperture tube top end interior said elongate cylinder for a predetermined distance, said thief conduit exiting said cylinder at a point on said cylinder below said open end.

9. The apparatus of claim 8 wherein said first thief opening is formed at substantially the same height with respect to said aperture tube top end as said aperture tube aperture.

10. The apparatus of claim 8 wherein said aperture tube has at least a first radius extending from the center thereof to said aperture tube and wherein said first thief opening is formed substantially radially opposite said aperture tube aperture.

11. The apparatus of claim 1 wherein said thief conduit is an elongate cylinder positioned in said aperture tube, said thief conduit opening through said aperture tube exterior surface at opposite ends of the thief conduit.

12. The apparatus of claim 11 wherein said thief conduit and aperture tube are glass.

* * * * *

UNITED STATES PATENT AND TRADEMARK OFFICE
CERTIFICATE OF CORRECTION

PATENT NO. : 3,930,736
DATED : January 6, 1976
INVENTOR(S) : Wallace H. Coulter

It is certified that error appears in the above-identified patent and that said Letters Patent are hereby corrected as shown below:

Column 2, line 18, change "the" to -- The --.

Column 3, line 52, change "Refferring" to -- Referring --.

Column 4, line 47, change "an" to -- An --.

Column 5, line 3, change "the" to -- The --.

Column 5, line 5, change "veing" to -- being --.

Column 5, line 8, change "the" to -- The --.

Signed and Sealed this twenty-second Day of June 1976

[SEAL]

Attest:

RUTH C. MASON
*Attesting Officer*

C. MARSHALL DANN
*Commissioner of Patents and Trademarks*